United States Patent
Dogo-Isonagie et al.

(10) Patent No.: US 12,214,063 B2
(45) Date of Patent: Feb. 4, 2025

(54) PEROXYMONOSULFATE WHITENING STRIPS

(71) Applicant: Colgate-Palmolive Company, New York, NY (US)

(72) Inventors: Cajetan Dogo-Isonagie, Mount Laurel, NJ (US); Suman Chopra, Monroe, NJ (US); Xiang Chen, Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 17/675,285

(22) Filed: Feb. 18, 2022

(65) Prior Publication Data

US 2022/0265523 A1 Aug. 25, 2022

Related U.S. Application Data

(60) Provisional application No. 63/151,239, filed on Feb. 19, 2021.

(51) Int. Cl.
| | | |
|---|---|---|
| *A61K 8/02* | (2006.01) | |
| *A61C 19/06* | (2006.01) | |
| *A61K 8/22* | (2006.01) | |
| *A61K 8/23* | (2006.01) | |
| *A61K 8/24* | (2006.01) | |
| *A61K 8/81* | (2006.01) | |
| *A61K 8/86* | (2006.01) | |
| *A61Q 11/00* | (2006.01) | |

(52) U.S. Cl.
CPC .......... *A61K 8/0237* (2013.01); *A61C 19/066* (2013.01); *A61K 8/22* (2013.01); *A61K 8/23* (2013.01); *A61K 8/24* (2013.01); *A61K 8/8147* (2013.01); *A61K 8/8176* (2013.01); *A61K 8/8182* (2013.01); *A61K 8/86* (2013.01); *A61Q 11/00* (2013.01); *A61K 2800/30* (2013.01); *A61K 2800/594* (2013.01); *A61K 2800/87* (2013.01)

(58) Field of Classification Search
CPC ... A61K 8/02; A61K 8/23; A61K 8/22; A61K 8/0237; A61K 8/24; A61Q 11/00
USPC .............................................. 424/48, 49, 53
See application file for complete search history.

(56) References Cited

U.S. PATENT DOCUMENTS

| | | |
|---|---|---|
| 3,337,466 A | 8/1967 | Puetzer |
| 3,556,711 A | 1/1971 | Stalter |
| 3,666,399 A | 5/1972 | Castrantas |
| 4,024,636 A | 5/1977 | Colpitts et al. |
| 4,062,793 A | 12/1977 | Schodel |
| 4,115,293 A | 9/1978 | Schoenholz et al. |
| 4,273,759 A | 6/1981 | Gaffar et al. |
| 4,292,211 A | 9/1981 | Herman |
| 4,309,410 A | 1/1982 | Gaffar |
| 4,612,191 A | 9/1986 | Yeh et al. |
| 4,886,669 A | 12/1989 | Ventouras |
| 4,971,782 A | 11/1990 | Rudy et al. |
| 5,032,178 A | 7/1991 | Cornell |
| 5,240,697 A | 8/1993 | Norfleet et al. |
| 5,736,158 A | 4/1998 | Quast |
| 5,882,630 A | 3/1999 | Gates et al. |
| 5,885,554 A | 3/1999 | Michael et al. |
| 5,939,080 A | 8/1999 | Michael et al. |
| 6,106,861 A | 8/2000 | Chauveau et al. |
| 6,264,703 B1 | 7/2001 | Coope |
| 6,274,122 B1 | 8/2001 | McLaughlin |
| 6,596,311 B1 | 7/2003 | Dobetti |
| 6,743,443 B1 | 6/2004 | Furitsu et al. |
| 6,811,793 B2 | 11/2004 | Wehling |
| 7,018,622 B2 | 3/2006 | Goodhart et al. |
| 7,501,409 B2 | 3/2009 | Murakami et al. |
| 7,641,892 B2 | 1/2010 | Gebreselassie et al. |
| 7,815,897 B1 | 10/2010 | Wehling et al. |
| 8,211,407 B2 | 7/2012 | Deckner et al. |
| 8,377,995 B2 | 2/2013 | Ikeda et al. |
| 8,741,269 B2 | 6/2014 | Mandadi et al. |
| 9,682,256 B2 | 6/2017 | Boyd et al. |
| 9,724,280 B2 | 8/2017 | Fei |
| 9,789,048 B2 | 10/2017 | Prencipe et al. |
| 2004/0120903 A1* | 6/2004 | Sagel ............... A61Q 11/00 424/53 |
| 2005/0169986 A1 | 8/2005 | Tian et al. |
| 2006/0034780 A1 | 2/2006 | Guan et al. |
| 2006/0073174 A1* | 4/2006 | Moro ............... A61K 9/7015 424/400 |
| 2006/0147394 A1 | 7/2006 | Shastry et al. |
| 2007/0071695 A1 | 3/2007 | Chopra et al. |
| 2007/0138674 A1 | 6/2007 | Anastasiou et al. |

(Continued)

FOREIGN PATENT DOCUMENTS

| | | |
|---|---|---|
| BE | 1020399 | 9/2013 |
| CN | 1170349 | 1/1998 |

(Continued)

OTHER PUBLICATIONS

Dupont, "Oxone Monopersulfate Compound." http://waterguardinc.com. Published online Jul. 1, 2014. (Year: 2014).*

Ispcorp.com (product brochure), "Polyplasdone Corspovidone." http://www.ispcorp.com/products/pharma/content/brochure/polycros/intro.html two (2) pages (Year: 2004).

Rivas, et al., "Catalytic Decomposition of Potassium Monopersulfate. Influence of Variables." Int. Scholarly Sci. Res. & Innovation 3(9): 476-80 (2009).

(Continued)

*Primary Examiner* — Walter E Webb

(57) ABSTRACT

The present disclosure provides a tooth whitening strip comprising a hydratable adhesive film comprising an inorganic salt of peroxymonosulfate, preferably an alkali metal salt or alkaline earth metal salt, or mixtures thereof, and methods of using the same.

11 Claims, No Drawings

(56) References Cited

U.S. PATENT DOCUMENTS

| | | |
|---|---|---|
| 2008/0050398 A1 | 2/2008 | Bockmuehl et al. |
| 2008/0260660 A1 | 10/2008 | Engelbrecht et al. |
| 2008/0274066 A1 | 11/2008 | Montgomery |
| 2009/0010970 A1 | 1/2009 | Velada |
| 2009/0175917 A1 | 7/2009 | Engelbrecht et al. |
| 2009/0208543 A1 | 8/2009 | Nathoo |
| 2012/0029135 A1 | 2/2012 | Kim et al. |
| 2012/0282192 A1 | 11/2012 | Miller |
| 2014/0377194 A1 | 12/2014 | Strand et al. |
| 2016/0296433 A1 | 10/2016 | Chen et al. |
| 2017/0014320 A1 | 1/2017 | Chen et al. |

FOREIGN PATENT DOCUMENTS

| | | |
|---|---|---|
| CN | 1528660 | 9/2004 |
| CN | 101163523 | 4/2008 |
| CN | 101360464 | 2/2009 |
| CN | 101404976 | 4/2009 |
| CN | 102802732 | 11/2012 |
| CN | 104367487 | 2/2015 |
| CN | 105764474 | 7/2016 |
| CN | 105792799 | 7/2016 |
| CN | 105792896 | 7/2016 |
| CN | 109689165 | 4/2019 |
| EP | 0045826 | 2/1982 |
| EP | 0157464 | 10/1987 |
| EP | 0248936 | 12/1987 |
| EP | 1736135 | 12/2006 |
| EP | 2700396 | 2/2014 |
| GB | 1374105 | 11/1974 |
| JP | H07-109212 | 4/1995 |
| JP | 2007-112761 | 5/2007 |
| KR | 20060081532 | 7/2006 |
| KR | 20060082532 | 7/2006 |
| RU | 2320315 | 3/2008 |
| RU | 2339361 | 11/2008 |
| RU | 2581906 | 4/2016 |
| WO | 1996/019193 | 6/1996 |
| WO | 2000/009079 | 2/2000 |
| WO | 2000/016737 | 3/2000 |
| WO | 2001/068045 | 9/2001 |
| WO | 2005/011582 | 2/2005 |
| WO | 2008/008617 | 1/2008 |
| WO | 2009/133525 | 11/2009 |
| WO | 2010/115037 | 10/2010 |
| WO | 2011/079167 | 6/2011 |
| WO | 2014/092732 | 6/2014 |
| WO | 2015/084296 | 6/2015 |
| WO | 2016/064882 | 4/2016 |
| WO | 2017/106067 | 6/2017 |
| WO | 2017/112672 | 6/2017 |
| WO | 2018/093356 | 5/2018 |
| WO | 2020/091808 | 5/2020 |
| WO | 2022/178240 | 8/2022 |

OTHER PUBLICATIONS

Anonymous, 2015, "Whitening Treatments", Mintel Database GNPD AN: 3224601.
Anonymous, 2020, "Teeth Whitening System", Mintel Database GNPD AN: 7941335.
International Search Report and the Written Opinion of the International Searching Authority issued in International Application PCT/US2022/016958 mailed May 27, 2022.
International Search Report and Written Opinion of the International Searching Authority in International Application No. PCT/US2016/062124, mailed Feb. 22, 2017.
International Search Report and Written Opinion of the International Searching Authority in International Application No. PCT/US2016/067784, mailed Mar. 10, 2017.
greenfootsteps.com; (Oct. 2, 2019) The Best Whitening Toothpastes for Health and the Environment [retrieved from internet] http://www.greenfootsteps.com/best-whitening-toothpastes.html.
International Search Report and the Written Opinion of the International Searching Authority issued in International Application PCT/US2023/028021 mailed on Oct. 19, 2023.

\* cited by examiner

PEROXYMONOSULFATE WHITENING STRIPS

CROSS-REFERENCE TO RELATED APPLICATIONS

This application claims priority to and the benefit of U.S. Provisional Application No. 63/151,239, filed on Feb. 19, 2021, the contents of which are hereby incorporated by reference in its entirety.

BACKGROUND

Consumer products providing for teeth whitening are numerous and take many forms, but one of the more popular forms are dental whitening strips. These strips, commonly with an adhesive material, are typically adhered to the anterior surface of the teeth for a prolonged period of time, such as 10 minutes or more, during which time an entrained whitening agent diffuses into the tooth enamel to bleach away stains. Such strips are often more convenient and more effective than alternative at-home whitening treatments, such as toothpastes and mouthwashes, because of the prolonged contact provided between the teeth and the whitening composition.

Products that are presently available to whiten teeth include a variety of different ingredients, and the primary active ingredient is most commonly a peroxide source such as hydrogen peroxide. The use of peroxide agents often presents numerous difficulties in both formulation and long-term stability of the resulting compositions. In addition, in high concentrations, or in prolonged contact with the oral mucosa, hydrogen peroxide can be highly irritating to the teeth and gums. Thus, alternative oxidizing agents with improved stability are needed, especially for whitening products which provide long-term contact with oral tissues.

Peroxysulfuric acid, and its salts, the peroxysulfates, are powerful oxidizing and stain removing agents. They are currently used for a variety of industrial and consumer purposes, including swimming pool treatment and denture cleaning. Peroxysulfate whitening products have been explored for some oral care applications, such as mouthwashes and toothpastes. The most common peroxymonosulfate oxidizing agent is potassium peroxymonosulfate, commonly referred The use of potassium monoperoxysulfate in oral care applications has been very limited by its instability in aqueous solution, especially in aqueous solution near or above neutral pH. Potassium monoperoxysulfate has been known to degrade even in the presence of small quantities of water and heat. Thus, potassium monoperoxysulfate whitening compositions face particular difficulties in formulations intended for anything more than transient or momentary use in the oral cavity.

There is thus a need for tooth whitening products which provide the convenience and duration of a strip with improved properties of peroxysulfate whitening agents.

BRIEF SUMMARY

The present disclosure provides a tooth whitening strip comprising a hydratable adhesive film comprising an inorganic salt of peroxymonosulfate, preferably an alkali metal salt or alkaline earth metal salt, or mixtures thereof.

Further areas of applicability of the present disclosure will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Open terms such as "include," "including," "contain," "containing" and the like mean "comprising." In this description, unless otherwise stated, the use of the singular also includes the plural. For example, "a lubricant" also comprehends the case where more than one lubricant is used In a first aspect, the present disclosure provides a tooth whitening strip (Strip 1) comprising a hydratable adhesive film comprising an inorganic salt of peroxymonosulfate, preferably an alkali metal salt or alkaline earth metal salt, or mixtures thereof. In further embodiments, the present disclosure provides:

1.1. Strip 1, wherein the inorganic salt of peroxymonosulfate is sodium peroxymonosulfate, potassium peroxymonosulfate, or lithium peroxymonosulfate, or a combination thereof;
1.2. Strip 1 or 1.1, wherein the salt of peroxymonosulfate is potassium peroxymonosulfate;
1.3. Strip 1.2, wherein the potassium peroxymonosulfate is provided as a triple salt of potassium peroxymonosulfate, potassium hydrogen sulfate and potassium sulfate, optionally wherein the triple salt comprises about 45%-50% by weight of potassium peroxymonosulfate, e.g., 47% or 49% by weight of potassium peroxymonosulfate;
1.4. Any of the preceding strips, wherein the strip comprises an effective amount of peroxymonosulfate salt which is 0.01% to 5%, by weight of the strip, e.g., 0.05% to 5%, or 0.1% to 5%, or 0.5% to 3%, or 0.5% to 2.5%, or 0.5 to 2%, or 0.5 to 1.5%, or 0.75 to 1.25%, or about 1%, by weight of the composition;
1.5. Any of the preceding strips, wherein the strip further comprises a second inorganic salt of peroxymonosulfate;
1.6. Any of the preceding strips, wherein the inorganic peroxymonosulfate salt is not particulated (e.g., not granulated);
1.7. Any of the preceding strips, wherein the strip does not comprise hydrogen peroxide;
1.8. Any of the preceding strips, wherein the strip does not comprise any of hydrogen peroxide, urea peroxide, peroxide salts (e.g., sodium peroxide, potassium peroxide, lithium peroxide, calcium peroxide), peroxy acids (e.g., peroxyacetic acid, peroxybenzoic acid, or salts or derivatives thereof), organic peroxides (e.g., urea hydrogen peroxide, glyceryl hydrogen peroxide, peroxy esters, diacyl peroxides, monoperoxyphthalate, or salt thereof), perborate salts, persilicate salts, percarbonate salts, chlorinated oxidizing agents (e.g., hypochlorite salts, chlorite salts, chlorate salts, perchlorate salts, chlorine dioxide);

1.9. Any of the preceding strips, wherein the inorganic salt of peroxymonosulfate is the only oxidizing agent present in the strip;

1.10. Strip 1.9, wherein potassium peroxymonosulfate (e.g., as part of a triple salt mixture) is the only oxidizing agent present in the strip;

1.11. Strip 1, or any of 1.1-1.10, wherein the hydratable adhesive film comprises one or more water-soluble or water-swellable polymers, including anionic polymers and/or neutral polymers;

1.12. Strip 1.11, wherein the hydratable adhesive film comprises from 50 to 99% by weight of water-soluble or water-swellable polymers, for example, 50 to 90% by weight, or 60 to 90% by weight, or 70 to 90% by weight, or 80-90% by weight;

1.13. Strip 1, or any of 1.1-1.12, wherein the hydratable adhesive film comprises one or more of: polyethylene glycols (such as PEG-200, PEG-300, PEG-400, PEG-500, PEG-600, PEG-800, PEG-1000, PEG-1600, PEG-2000), polypropylene glycols, polysaccharides (e.g., cellulose derivatives, for example carboxymethyl cellulose, hydroxyethyl cellulose, hydroxypropyl cellulose, hydroxypropyl methyl cellulose, ethyl cellulose, microcrystalline cellulose; or polysaccharide gums, for example xanthan gum, guar gum, or carrageenan gum, pectins, karaya gum); chitosans; dextrans; polyvinyl pyrrolidone (PVP), such as cross-linked PVP; hyaluronic acid and sodium hyaluronates; synthetic anionic polymeric polycarboxylates, such as copolymers of maleic anhydride or acid with another polymerizable ethylenically unsaturated monomer, preferably methyl vinyl ether (e.g., copolymers in a 1:4 to 4:1 ratio of maleic anhydride/acid to methyl vinyl ether); polyphosphonic acids and polyphosphonates (i.e., polyphosphoesters); cross-linked carboxyvinyl copolymers; polyacrylic acid or polyacrylate polymers; polyacrylamides, such as (2-hydroxypropyl)methacrylamide; polyoxyethylene-polyoxypropylene copolymers (PEG-PPG), including block copolymers, triblock copolymers (poloxamers, such as poloxamer 407), and random copolymers, such as PEG/PPG-116/66 and PEG/PPG-38/8; polyamines; polyvinyl alcohols; polyvinyl pyrrolidine-polyvinyl acetate copolymers (PVP-VA); polyoxazolines, such as poly(2-alkyl-2-oxazolines), e.g., methyl, ethyl, or isopropyl substituted polyoxazolines; and quaternary ammonium polymers;

1.14. Strip 1, or any of 1.1-1.13, wherein the hydratable adhesive film comprises one or more of: polyethylene glycol polymers (PEG), polyacrylic acid or polyacrylate polymers (PAA), polyvinylpyrrolidone polymers (PVP), polyvinylpyrrolidone-vinyl acetate copolymers (PVP-VA), polyoxazoline polymers (PO), polyoxyethylene-polyoxypropylene (PEG-PPG) block copolymers, and mixtures thereof;

1.15. Strip 1.14, wherein the hydratable adhesive film comprises at least one of each of:

a polyethylene glycol polymer, a polyacrylic acid or polyacrylate polymer, a polyvinylpyrrolidone polymer, a polyvinylpyrrolidone-vinyl acetate copolymer, a polyoxazoline polymer, and a polyoxyethylene-polyoxypropylene copolymer;

1.16. Strip 1, or any of 1.1-1.13, wherein the hydratable adhesive film comprises at least one of: a cellulose derivative (e.g., carboxymethyl cellulose, hydroxyethyl cellulose, hydroxypropyl cellulose, hydroxypropyl methyl cellulose, or ethyl cellulose), a polyethylene glycol polymer (PEG), a polyacrylic acid or polyacrylate polymer (PAA), a polyvinylpyrrolidone polymer (PVP), a polyvinylpyrrolidone-vinyl acetate copolymer (PVP-VA), a polyoxazoline polymer (PO), a polyoxyethylene-polyoxypropylene (PEG-PPG) block copolymer, or mixtures thereof;

1.17. Strip 1, or any of 1.1-1.16, wherein the hydratable adhesive film comprises 60 to 90% by weight of any of said polymers or mixtures of polymers, e.g., 70 to 90% by weight or 80 to 90% by weight;

1.18. Strip 1, or any of 1.1-17, wherein the hydratable adhesive film adheres to the surface of the teeth after becoming wetted with water or saliva or assisting solvent;

1.19. Strip 1, or any of 1.1-1.18, wherein the strip further comprises a polyphosphate or an organic cyclic polyphosphate, such as an alkali metal pyrophosphate, an alkali metal tripolyphosphate, an alkali metal tetraphosphate, an alkali metal hexametaphosphate, an alkali metal insoluble metaphosphate, an alkali metal phytic acid salt, or a mixture thereof;

1.20. Strip 1.19, wherein the strip comprises sodium or potassium pyrophosphate (e.g., tetrasodium or tetrapotassium pyrophosphate and/or disodium or dipotassium pyrophosphate), sodium or potassium tripolyphosphate, sodium or potassium tetraphosphate, sodium or potassium phytic acid salt, or a mixture thereof;

1.21. Strip 1.19 or 1.20, wherein the strip comprises from 0.1 to 5% by weight of polyphosphates, e.g., 0.5 to 3%, or 1% to 2.5%, or 1.5% to 2.5% or about 2% by weight of polyphosphates;

1.22. Strip 1, or any of 1.1-1.21, wherein the strip further comprises a desensitizing agent, e.g., in an amount from 0.1 to 5% by weight, such as potassium nitrate;

1.23. Strip 1, or any of 1.1-1.22, wherein the strip further comprises an enamel strengthening agent, e.g., in an amount from 0.1 to 5% by weight, such as zinc phosphate;

1.24. Strip 1 or any of 1.1-1.23, wherein the strip further comprises one or more of flavors and sweeteners;

1.25. Strip 1 or any of 1.1-1.24, wherein the strip is substantially anhydrous (e.g., less than 4%, or less than 3%, or less than 2%, or less than 1 t% water by weight);

1.26. Strip 1 or any of 1.1-1.25, wherein the hydratable adhesive film of the strip consists of:

| Ingredient in Film | Weight of Dry Film % |
| --- | --- |
| One or more polymers, e.g.., PVP, PVP-VA, PO, PAA, PEG-PPG copolymer (e.g., poloxamer), HEC, HPC, HPMC, CMC, and/or PEG | 40-95% (e.g., 75-90%) |
| Polyphosphates (e.g., pyrophosphates) | 1-5% (e.g., 2%) |
| MPS Triple Salt ($2KHSO_5 \cdot KHSO_4 \cdot K_2SO_4$) | 0.5-10% (e.g., 2-2.2%) (0.25-5% MPS, e.g., 1% MPS) |
| Sweeteners | 0.5-5% (e.g., 1.8%) |
| Flavors | 0.5-5% (e.g., 2%) |
| Total | ca. 100 |

1.27. Strip 1 or any of 1.1-1.255, wherein the hydratable adhesive film of the strip consists of:

| Ingredient in Film | Weight of Dry Film % |
|---|---|
| PVP/ PVP-VA copolymer/PO | 40-80% (e.g., 60%) |
| PAA | 1-15% (e.g., 5%) |
| PEG-PPG block copolymer/ PEG (e.g., PEG-600) | 10-40% (e.g., 24%) |
| Polyphosphates (e.g., pyrophosphates) | 1-5% (e.g., 2%) |
| MPS Triple Salt ($2KHSO_5 \cdot KHSO_4 \cdot K_2SO_4$) | 0.5-10% (e.g., 2-2.2%) (0.25-5% MPS, e.g., 1% MPS) |
| Sweeteners | 0.5-5% (e.g., 1.8%) |
| Flavors | 0.5-5% (e.g., 2%) |
| Total | ca. 100 |

1.28. Strip 1, or any of 1.1-1.27, wherein hydratable adhesive film of the strip is prepared as an aqueous suspension or aqueous/alcoholic suspension and subsequently dried onto a backing layer to provide the strip;

1.29. Strip 1, or any of 1.1-1.28, wherein the inorganic salt of peroxymonosulfate is dispersed or entrained throughout the hydratable adhesive polymer film of the strip;

1.30. Strip 1, or any of 1.1-1.25, wherein the strip further comprises an inert removable paper or plastic protective film and/or an affixed inert paper or plastic backing strip and wherein said protective film or backing strip is adhered to the hydratable adhesive film, optionally, wherein the protective film and/or the backing strip are comprises of wax paper, coated paper, treated paper, polyethylene, polypropylene, polyvinyl chloride, polyvinyl acetate, polymethyl methacrylate, polytetrafluoroethylene, polyesters (e.g., polyethylene terephthalate), polyimides, polycarbonates, or any combination thereof;

1.31. Strip 1, or any of 1.1-1.30, wherein the strip consists of the hydratable polymer film with one affixed inert paper or plastic backing and one removable inert paper or plastic backing 1.32. Strip 1, or any of 1.1-1.31, wherein the strip provides whitening of the teeth for a period of time of at least 10 minutes, e.g., 10 minutes to 30 minutes, or 10 minutes to 60 minutes;

1.33. Strip 1, or any of 1.1-1.32, wherein the strip measures from 1 cm to 15 cm in length and from 0.5 to 2 cm in width, and from 0.1 to 5 mm in thickness.

1.34. Strip 1, and any of 1.1-1.5 or 1.8-1.33, wherein the strip comprises a whitening agent in addition to the inorganic salt of peroxymonosulfate.

1.35. Strip 1.34, wherein the additional whitening agent comprise a peroxide whitening agent, comprising a peroxide compound.

1.36. Strip 1.35, wherein the peroxide compound is an oxidizing compound comprising a bivalent oxygen-oxygen group.

1.37. Strip 1.35 or 1.36, wherein the peroxide compound is selected from the group consisting of: include hydrogen peroxide, peroxides of alkali and alkaline earth metals, organic peroxy compounds, peroxy acids, pharmaceutically-acceptable salts thereof, and mixtures thereof.

1.38. Strip 1.37, wherein peroxides of alkali and alkaline earth metals are selected from the group consisting of: lithium peroxide, potassium peroxide, sodium peroxide, magnesium peroxide, calcium peroxide, barium peroxide, and mixtures thereof.

1.39. Strip 1.37, wherein the organic peroxy compounds are selected from the group consisting of: carbamide peroxide (also known as urea hydrogen peroxide), glyceryl hydrogen peroxide, alkyl hydrogen peroxides, dialkyl peroxides, alkyl peroxy acids, peroxy esters, diacyl peroxides, benzoyl peroxide, and monoperoxyphthalate, and mixtures thereof.

1.40. Strip 1.37, wherein peroxy acids and their salts are selected from the group consisting of: organic peroxy acids such as alkyl peroxy acids, and monoperoxyphthalate and mixtures thereof, as well as inorganic peroxy acid salts such as persulfate, dipersulfate, percarbonate, perphosphate, perborate and persilicate salts of alkali and alkaline earth metals such as lithium, potassium, sodium, magnesium, calcium and barium, and mixtures thereof.

1.41. Strip 1.34, wherein the whitening agent comprises hydrogen peroxide, or urea peroxide, or sodium percarbonate and mixtures thereof.

1.42. Strip 1.34, wherein the peroxide compound comprises hydrogen peroxide.

1.43. Strip 1.34, wherein the whitening agent is a non-peroxide whitening agent.

1.44. Strip 1.43, wherein the non-peroxide whitening agents include is selected from the group consisting of: non-peroxy compounds (e.g., such as chlorine dioxide), chlorites, hypochlorites. And colorants (e.g., titanium dioxide and hydroxyapatite).

As used herein, the term "strip" refers to a solid, pliable, adherent material which comprises a single-layer hydratable film comprising an inorganic peroxymonosulfate salt entrained or dispersed in a polymer matrix, and optionally a backing for the front and/or rear surfaces of the film. The film, after wetting with water or saliva or assisting solvent, and upon adherence to the surface of the teeth, provides an aqueous vehicle which permits the inorganic peroxymonosulfate salt to diffuse towards the surface of the teeth to provide an oxidative whitening effect on the teeth.

In one embodiment, the peroxymonosulfate is potassium peroxymonosulfate (also known as MPS, potassium monopersulfate). The potassium peroxymonosulfate (an example of which is Caroat® or Oxone®, an oxidizing agent) may be combined to form or exist as a triple salt of potassium peroxymonosulfate, potassium hydrogen sulfate and potassium sulfate ($2KHSO_5 \cdot KHSO_4 \cdot K_2SO_4$).

Potassium peroxymonosulfate has limited stability in aqueous solutions and can be stabilized by other common toothpaste ingredients. Therefore, contact with water during processing and storage should be avoided or minimized. The strip is preferably packaged in a moisture free environment. Preferably, strips are individually packaged and sealed into unit dose packages. The strips are typically stored in an air tight, moisture-proof package, e.g., sachets, sealed metal foil pouches, blister packs, and desiccant capped tubes. Useful packaging materials include polymeric packaging (e.g., polyethylene and polypropylene), metal foil packaging (e.g., aluminum), and combinations thereof.

The strips of the present disclosure contain no water or have a low water content. As used herein, the term "low water content" means the total concentration of water, including any free water and all water contained in any ingredients. In various embodiments of the composition, the amount of water is in an amount of less than 4% by weight, or less than 3% by weight, or less than 2% by weight, or less than 1% by weight, or less than 0.5% by weight, or less than 0.1%, or about 0.0001% to about 4% by weight, or about 0.0001% to about 0.5% by weight or about 0.0001% to about 0.1% by weight.

The amount of peroxymonosulfate salt, e.g., potassium peroxymonosulfate, in the strips of the invention is effective to result in improved tooth whitening when used once or twice daily for about three months as compared to a control strip without the peroxymonosulfate salt. The amount of peroxymonosulfate salt typically is about 0.1% to about 10%, by weight of the composition.

In some embodiments, the compositions of the present disclosure contain a buffering agent. Examples of buffering agents include anhydrous carbonates such as sodium carbonate, sesquicarbonates, bicarbonates such as sodium bicarbonate, silicates, bisulfates, phosphates such as monopotassium phosphate and dipotassium phosphate, citrates, pyrophosphates (sodium and potassium salts) and combinations thereof. The amount of buffering agent is sufficient to provide a pH of about 5 to about 9, preferable about 6 to about 8, and more preferable about 7, when the strip is hydrated. Typical amounts of buffering agent are about 0.1% to about 5%, in one embodiment about 1% to about 3%, in another embodiment about 0.5% to about 1%, by weight of the total composition.

The compositions of the present disclosure optionally contain a binder, preferably a polymeric binder, which is compatible with an oxidizing agent, which adds bulk to the hydratable film, and assists in holding the components of the film together in the form of a strip. Examples of suitable polymeric binders include, e.g., starches, natural gums, (e.g., xanthan gum), cellulose gums, microcrystalline cellulose, maltodextrins, methylcellulose, cellulose ethers, sodium carboxymethylcellulose, ethylcellulose, gelatin, polyethylene glycol, polyvinylpyrrolidone, pectins, alginates, polyacrylamides, polyvinyloxazolidone, polyvinyl alcohols and mixtures thereof. The binder can also comprise one or more non-polymeric binders such as dextrose, lactose, sucrose, sorbitol, mannitol, xylitol and the like. Typically, the binder is present in the composition in an amount of about 0.1% by weight to about 30% by weight, about 1% by weight to about 10% by weight, or about 1% by weight to about 5% by weight.

In some embodiments, the strips comprise a poloxamer, which is a polyoxyethylene-polyoxypropylene triblock copolymer. For example, suitable poloxamers may include one or more of Pluronic® L35, Pluronic® L43, Pluronic® L64, Pluronic® L10, Pluronic® L44, Pluronic® L62, Pluronic® 10R5, Pluronic® 17R4, Pluronic® L25R4, Pluronic® P84, Pluronic® P65, Pluronic® PI 04, and Pluronic® PI 05. Pluronic® brand dispersants are commercially available from BASF, Florham Park, NJ.

In some embodiments, the strips of the present disclosure may comprise a cross-linked polyvinylpyrrolidone, also known as poly-N-vinyl-poly-2-pyrrolidone, and commonly abbreviated to cross-linked "PVP." PVP generally refers to a polymer containing vinylpyrrolidone (also referred to as N-vinylpyrrolidone, N-vinyl-2-pyrrolidinone and N-vinyl-2-pyrrolidinone) as a monomeric unit. The monomeric unit may include a polar imide group, four non-polar methylene groups, and a non-polar methane group. Cross linked PVP includes those commercially available as KOLLIDON® and LUVICROSS®, marketed by BASF, Mount Olive, N.J., USA; and POLYPLASDO E® INF-10, marketed by, Ashland, Covington, Kent., USA.

In some embodiments, a PVP copolymer is employed, such as a polyvinylpyrrolidone-vinyl acetate copolymer (PVP-VA) (e.g., commercially available as Plasdone S-630 from Ashland Inc.), a polyvinyl pyrrolidone-co-polyvinyl butyrate copolymer (PVP-VB), or a polyvinyl pyrrolidone-co-polyvinyl propionate copolymer (PVP-VP), or mixtures thereof.

The strips of the present disclosure can optionally contain whitening agents in addition to the peroxymonosulfate salt. Whitening agents are generally materials which are effective to provide whitening of a tooth surface to which it is applied, and include agents such as hydrogen peroxide and urea peroxide. In various embodiments, the compositions of the present disclosure may optionally comprise a peroxide whitening agent, comprising a peroxide compound. A peroxide compound is an oxidizing compound comprising a bivalent oxygen-oxygen group. Peroxide compounds include peroxides and hydroperoxides, such as hydrogen peroxide, peroxides of alkali and alkaline earth metals, organic peroxy compounds, peroxy acids, pharmaceutically-acceptable salts thereof, and mixtures thereof. Peroxides of alkali and alkaline earth metals include lithium peroxide, potassium peroxide, sodium peroxide, magnesium peroxide, calcium peroxide, barium peroxide, and mixtures thereof. Organic peroxy compounds include carbamide peroxide (also known as urea hydrogen peroxide), glyceryl hydrogen peroxide, alkyl hydrogen peroxides, dialkyl peroxides, alkyl peroxy acids, peroxy esters, diacyl peroxides, benzoyl peroxide, and monoperoxyphthalate, and mixtures thereof. Peroxy acids and their salts include organic peroxy acids such as alkyl peroxy acids, and monoperoxyphthalate and mixtures thereof, as well as inorganic peroxy acid salts such as persulfate, dipersulfate, percarbonate, perphosphate, perborate and persilicate salts of alkali and alkaline earth metals such as lithium, potassium, sodium, magnesium, calcium and barium, and mixtures thereof. In various embodiments, the peroxide compound comprises hydrogen peroxide, urea peroxide, sodium percarbonate and mixtures thereof. In some embodiments, the peroxide compound comprises hydrogen peroxide. In some embodiments, the peroxide compound consists essentially of hydrogen peroxide. In some embodiments a non-peroxide whitening agent may be provided. Whitening agents among those useful herein include non-peroxy compounds, such as chlorine dioxide, chlorites and hypochlorites. Chlorites and hypochlorites include those of alkali and alkaline earth metals such as lithium, potassium, sodium, magnesium, calcium and barium. Non-peroxide whitening agents also include colorants, such as titanium dioxide and hydroxyapatite. One or more additional whitening agents are optionally present in a tooth-whitening effective total amount. In some embodiments the compositions additionally comprise an activator, e.g., tetraacetylethylenediamine. In some embodiments, the strips of the present invention are free of all of the above enumerated additional whitening agents.

The strips of the present disclosure optionally can also include other ingredients, e.g., flavor agents; fillers; surfactants; preservatives, e.g., sodium benzoate and potassium sorbate; color agents including, e.g., dyes and pigments; and sweeteners.

Examples of the surfactant that can be used are sodium lauryl sulfate, sorbitan fatty acid ester, polyoxyethylene (20) sorbitan monooleate (Polysorbate 80 or Tween 80), polyethylene glycol fatty acid ester, polyoxyethylene sorbitan fatty acid ester, polyoxyethylene alkyl ether, polyoxyethylene polyoxypropylene alkyl ether, polyoxyethylene polyoxypropylene block copolymer, polyoxyethylene alkyl phenyl ether, polyoxyethylene castor oil, polyoxyethylene hydrogenated castor oil, polyoxyethylene sorbitol fatty acid ester and polyoxyethylene glycerol fatty acid ester. In the present invention, each of them may be used solely or two or more thereof may be used jointly. Typical amounts of surfactant are about 0.1% to about 3%, in one embodiment about 0.1% to about 2%, in another embodiment about 0.1% to about 1%, by weight of the total composition.

Examples of the filler are crystalline cellulose, ethylcellulose, dextrin, various kinds of cyclodextrin (α-cyclodextrin, β-cyclodextrin and γ-cyclodextrin), sodium sulfate, as well as derivatives thereof and pullulan.

Useful flavor agents include natural and synthetic flavoring sources including, e.g., volatile oils, synthetic flavor oils, flavoring aromatics, oils, liquids, oleoresins and extracts derived from plants, leaves, flowers, fruits, stems and combinations thereof. Suitable flavor agents include, e.g., citric oils, e.g., lemon, orange, grape, lime and grapefruit, fruit essences including, e.g., apple, pear, peach, grape, strawberry, raspberry, cherry, plum, pineapple, apricot, and other fruit flavors. Other useful flavor agents include, e.g., aldehydes and esters (e.g., benzaldehyde (cherry, almond)), citral, i.e., alpha-citral (lemon, lime), neral, i.e., beta-citral (lemon, lime), decanal (orange, lemon), aldehyde C-8 (citrus fruits), aldehyde C-9 (citrus fruits), aldehyde C-12 (citrus fruits), tolyl aldehyde (cherry, almond), 2,6-dimethyloctanal (green fruit), 2-dodedenal (citrus, mandarin) and mixtures thereof.

Suitable coloring agents include, e.g., food, drug and cosmetic (FD&C) colors including, e.g., dyes, lakes, and certain natural and derived colorants. Useful lakes include dyes absorbed on aluminum hydroxide and other suitable carriers.

Suitable sweetening agents include stevia, sugars such as sucrose, glucose, invert sugar, fructose, ribose, tagalose, sucralose, maltitol, erythritol, xylitol, and mixtures thereof, saccharin and its various salts (e.g., sodium and calcium salt of saccharin), cyclamic acid and its various salts, dipeptide sweeteners (e.g., aspartame), acesulfame potassium, dihydrochalcone, glycyrrhizin, and sugar alcohols including, e.g., sorbitol, sorbitol syrup, mannitol and xylitol, and combinations thereof.

It is understood that while general attributes of each of the above categories of materials may differ, there may be some common attributes and any given material may serve multiple purposes within two or more of such categories of materials. All of the ingredients in the compositions may have functions in addition to their primary function, and may contribute to the overall properties of the composition, including its stability, efficacy, consistency, mouthfeel, taste, odor and so forth. For example, a binder may also function as a disintegrating agent and vice versa.

In a second aspect, the present disclosure provides a method for whitening teeth comprising the steps of (a) wetting Strip 1, or any of Strips 1.1 et seq., or any other embodiments thereof, with water or saliva or assisting solvent (e.g., wetting the hydratable adhesive film), (b) removing any protective backing from the strip, and (c) affixing the adhesive surface of the strip to the teeth for a sufficient period of time (e.g., 10 to 60 minutes, or 10 to 30 minutes, or 10 to 20 minutes) to effect whitening of the teeth contacted by the wetted film.

In other embodiments, the present disclosure provides for use Strip 1, or any of Strips et seq., or any other embodiments thereof, for the whitening of the teeth.

EXAMPLES

Exemplary embodiments of the present disclosure will be illustrated by reference to the following examples, which are included to exemplify, but not to limit the scope of the present invention.

In the examples and elsewhere in the description of the invention, chemical symbols and terminology have their usual and customary meanings. Temperatures are in degrees Celsius unless otherwise indicated. The amounts of the components are in weight percent based on the standard described; if no other standard is described then the total weight of the composition is to be inferred. Various names of chemical components include those listed in the CTFA International Cosmetic Ingredient Dictionary (Cosmetics, Toiletry and Fragrance Association, Inc., $7^{th}$ ed. 1997).

EXAMPLE 1

Exemplary MPS-Based Whitening Strip

Potassium peroxymonosulfate is combined with a polymer matrix in an aqueous solution or suspension and mixed until homogenous. The resulting viscous or gel-like solution or suspension is then formed into a thin-layer film on an inert, plastic backing, such as polyethylene or polypropylene. The film is dried to remove water, followed by affixation of a removable protective backing, and cutting into strips.

The final dried strips have a composition as follows:

| Ingredient in Film | Weight of Dry Film % |
| --- | --- |
| Polyvinylpyrrolidone PVP, PVP Vinyl Acetate, and/or Polyoxazoline | 40-80% (e.g., 60%) |
| Carbomer (Carbopol 971) or Polyacrylic acid | 0-10% (e.g., 5%) |
| Polyoxypropylene-Polyoxyethylene Block Copolymer and/or PEG 600 | 0-30% (e.g., 24%) |
| Polyphosphates (e.g., sodium or potassium pyrophosphates) | 1-5% (e.g., 2%) |
| Potassium MPS triple salt ($2KHSO_5 \cdot KHSO_4 \cdot K_2SO_4$) | 1-10% (e.g., 2.2% (1% MPS)) |
| Sweeteners | 1-3% (e.g., 1.8%) |
| Flavor | 1-3% (e.g., 2%) |
| Total | 100 |

Other final strips may be prepared according to the same or similar method, providing, for example, strips having the following composition:

| Ingredient in Film | Weight of Dry Film % |
| --- | --- |
| PVP, PVP-VA, PO, PAA, PEG-PPG copolymer (e.g., poloxamer), HEC, HPC, HPMC, CMC, and/or PEG | 40-95% (e.g., 75-90%) |
| Polyphosphates (e.g., sodium or potassium pyrophosphates) | 1-5% (e.g., 2%) |
| Potassium MPS Triple Salt ($2KHSO_5 \cdot KHSO_4 \cdot K_2SO_4$) | 0.5-10% (e.g., 2-2.2%) (0.25-5% MPS, e.g., 1% MPS) |
| Sweeteners | 0.5-5% (e.g., 1.8%) |
| Flavors | 0.5-5% (e.g., 2%) |
| Total | ca. 100 |

The invention has been described above with reference to illustrative Examples, but it is to be understood that the invention is not limited to the disclosed embodiments. Alterations and modifications that would occur to one of skill in the art upon reading the specification are also within the scope of the invention, which is defined in the appended claims.

What is claimed is:

1. A tooth whitening strip comprising:
a hydratable adhesive film consisting of:
from about 60 to about 90%, by weight, of water-soluble or water-swellable polymers, the water-soluble or water-swellable polymers consisting of a polyvinylpyrrolidone polymer and a polyethylene glycol polymer;
from about 0.1 to about 10%, by weight, of an inorganic salt of peroxymonosulfate, the inorganic salt of peroxymonosulfate being dispersed in the hydratable adhesive film;
water; and
a buffering agent,
wherein all weight percentages are based on the total weight of the strip.

2. The strip of claim 1, wherein the inorganic salt of peroxymonosulfate is sodium peroxymonosulfate, potassium peroxymonosulfate, or ammonium peroxymonosulfate.

3. The strip of claim 1, wherein the inorganic salt of peroxymonosulfate is potassium peroxymonosulfate.

4. The strip of claim 3, wherein the potassium peroxymonosulfate is provided as a triple salt of potassium peroxymonosulfate, potassium hydrogen sulfate and potassium sulfate.

5. The strip of claim 4, wherein the strip comprises an effective amount of peroxymonosulfate salt which is 0.1 to 5%, by weight of the composition.

6. The strip of claim 1, wherein the strip does not comprise hydrogen peroxide.

7. The strip of claim 1, wherein the inorganic salt of peroxymonosulfate is the only oxidizing agent present in the strip.

8. The strip of claim 1, wherein the hydratable adhesive film comprises about 70 to about 90%, by weight, of the one or more polymers.

9. A method for whitening teeth comprising the steps of (a) wetting the strip according to claim 1, with water or saliva or assisting, (b) removing any protective backing from the strip, and (c) affixing the adhesive surface of the strip to the teeth for a sufficient period of time to effect whitening of the teeth contacted by the wetted film.

10. The strip of claim 1, wherein the triple salt of potassium peroxymonosulfate comprises about 45 about 50%, by weight, of the amount of potassium peroxymonosulfate.

11. A tooth whitening strip consisting of:
a hydratable adhesive film consisting of:
one or more polyvinylpyrrolidone polymer,
a polyethylene glycol,
an inorganic salt of peroxymonosulfate dispersed in the hydrated adhesive film,
a buffering agent, and
water;
an inert paper or plastic backing affixed to the hydratable adhesive film; and
a removable inert paper or plastic backing removably affixed to the hydratable adhesive film.

* * * * *